United States Patent [19]

Paoluccio

[11] Patent Number: 5,471,679
[45] Date of Patent: Dec. 5, 1995

[54] FACE PROTECTOR

[76] Inventor: John A. Paoluccio, P.O. Box J 5038 Salida Blvd., Salida, Calif. 95829

[21] Appl. No.: 920,631

[22] Filed: Jul. 27, 1992

[51] Int. Cl.⁶ .................................................... A61F 9/04
[52] U.S. Cl. ................................................................ 2/9
[58] Field of Search .................................. 2/9, 10, 11, 13, 2/15, 427, 429; 351/158; 24/305, 326, 335, 338, 457, 459, 460, 531, 486

[56] References Cited

U.S. PATENT DOCUMENTS

| | | | |
|---|---|---|---|
| 1,725,340 | 8/1929 | Castriotis | 2/10 |
| 3,946,466 | 3/1976 | Sakai | 2/10 |
| 3,991,753 | 11/1976 | Viesca y Viesca | 2/9 |
| 4,821,340 | 4/1989 | Johnson | 2/9 |
| 4,869,586 | 9/1989 | Chung | 351/158 |
| 4,872,465 | 10/1989 | Kuntz et al. | 2/9 |
| 4,924,526 | 5/1990 | Parissenti et al. | 2/9 |
| 4,944,039 | 7/1990 | Dietrich | 2/9 |
| 4,965,887 | 10/1990 | Paoluccio et al. | 2/9 |

FOREIGN PATENT DOCUMENTS

| | | | |
|---|---|---|---|
| 685696 | 11/1939 | Germany | 2/10 |
| 688227 | 1/1940 | Germany | 2/9 |
| 200635 | 7/1923 | United Kingdom | 2/10 |
| 513750 | 10/1939 | United Kingdom | 2/9 |

*Primary Examiner*—C. D. Crowder
*Assistant Examiner*—Michael A. Neas

[57] ABSTRACT

A face protector for protecting the face against fluid splatter or splash of bodily fluids as occurs in the medical field, which includes a glassless temple frame support with two reusable double clips that are slid over the temple frames and clamped onto the ends of a disposable clear plastic face shield lens. The two reusable double clips are then carefully slid into position on the temple frames of the glassless supporting frames. Once the face protector is adjusted to fit ones face the reusable double clips are locked by set screws onto the temple frames where they can remain in place. The disposable face shield lens can simply be removed, discarded and quickly replaced without further adjustment being necessary. This device thereby provides for practical face shield protection. When soiled, scratched or contaminated the clear face shield lens may be removed and discarded. The support frames with (reusable double clips) attached then act as the structural support of the face protector ready to receive a new clean face shield lens. In another form of the invention the reusable double clips can be attached to the wearers own prescription glasses or safety glasses thereby converting the assembly into a face protector. In yet another form of the invention the clips, lens and head cover are attached to a preformed support frame.

19 Claims, 8 Drawing Sheets

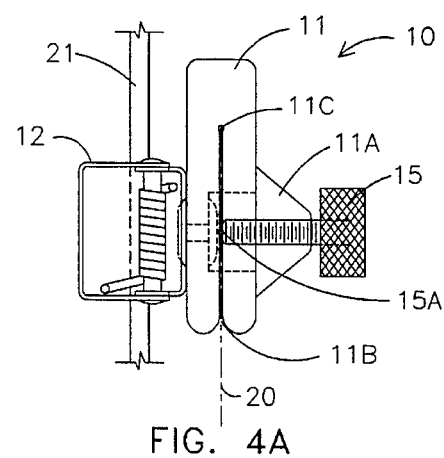
FIG. 4A
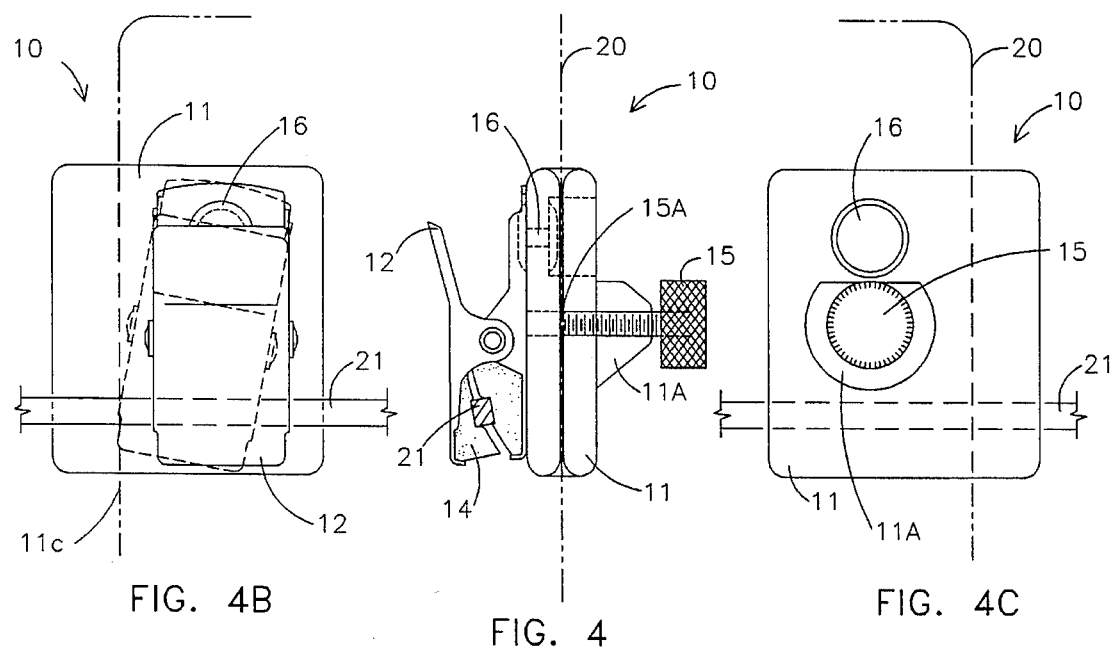
FIG. 4B
FIG. 4
FIG. 4C

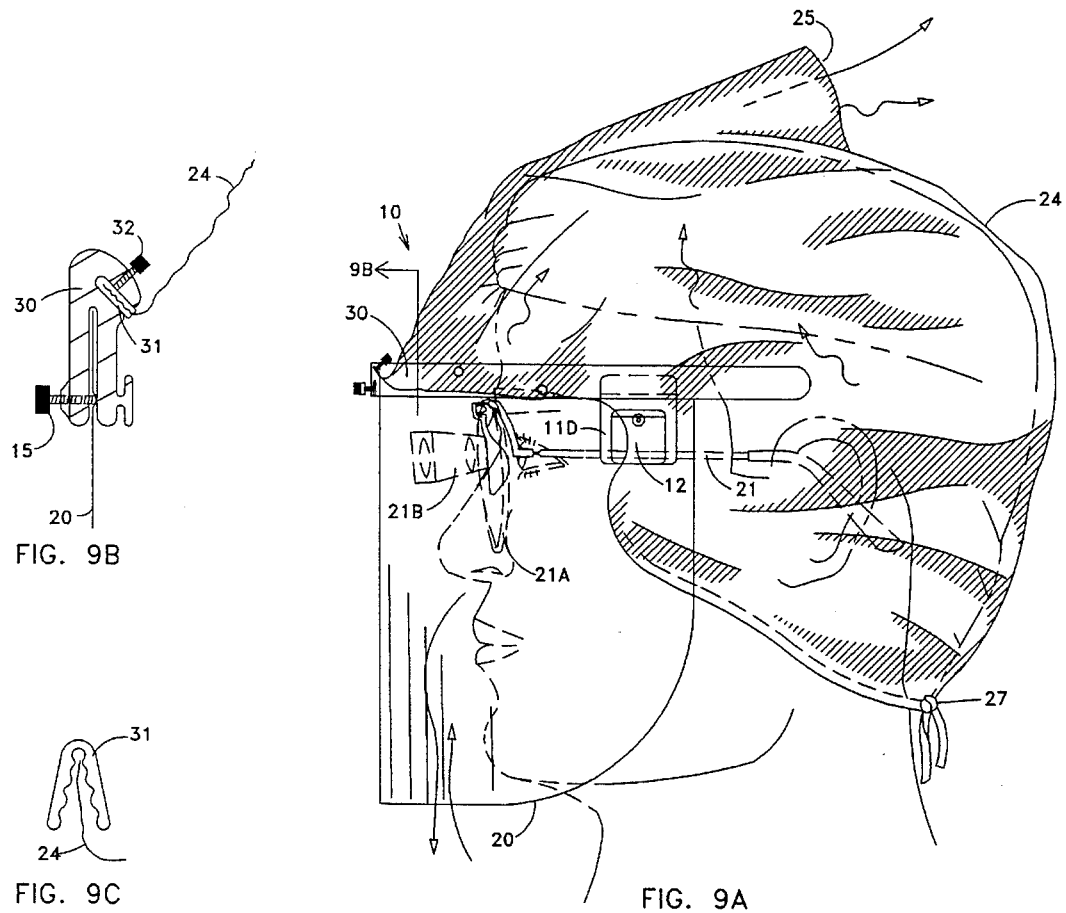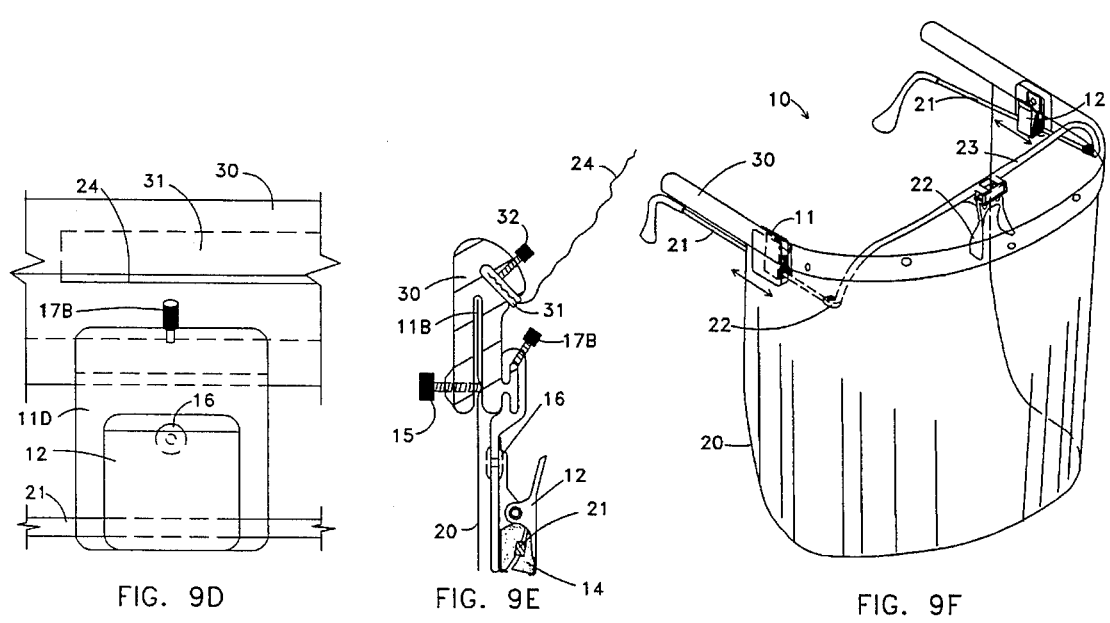

FACE PROTECTOR

BACKGROUND OF THE INVENTION

The invention relates to apparatus to prevent splash and spatter of bodily fluids on health care workers in dentistry and other medical fields.

Prior art devices have either been uncomfortable, bulky, obtrusive, costly, difficult to adjust, or difficult to clean and sterilize. New OSHA regulations require that chin length face shields be used by those that may be exposed to the splash or spatter of bodily fluids as may occur in the dental or medical field.

Extensive cleaning and sterilization procedures are required to prevent contamination that further increases the cost of health care. The use of disposable products in medical facilities is increasing because it is less expensive, in many cases, to replace a low cost product than incur the cost of labor for cleaning and sterilization.

Frequently, a doctor may need to wear magnifying lens or other attachments to his glasses during certain procedures that interfere with conventional face shield use. This is a major design consideration.

The prior art structures include U.S. Pat. No. 4,965,887 having a joint inventor that is the same as the present invention. While the apparatus described in that patent is useful for many applications it and other prior art suffers from the following disadvantages:

1. The clips are discarded with the shield which is wasteful and results in a poor use of natural resources.
2. The cost is very high because of the waste of material and the high labor content.
3. The present shields are limited in adjustment in their present form to horizontal adjustment along the temple members of a frame.
4. Each time a typical prior art shield is washed, sterilized and placed back on the wearer's glasses the mounting brackets have to be adjusted. This is particularly significant when the health care professional visits a number of patients. When the brackets are adjusted improperly, as could happen if the wearer were to hurry, the shield may be installed in a crooked position and may not provide proper protection.
5. The present face protection devices are very difficult to clean and sterilize when the user goes from patient to patient. The new OSHA guidelines for those exposed to bodily fluids such as might occur in dentistry and the medical field, require frequent changing of face shields. Disposable shields are being required in more and more medical procedures because of the high cost and time required for proper cleaning and sterilizing for contamination prevention between patients.
6. The present face shield devices are not practical to recycle as they contain combinations of different materials such as plastics and metal.
7. Prior art apparatus commonly uses head covers for added protection along with greater side protection at the eye area. Replacing head covers and face shields between patients creates an expensive practice with first cost, installation and adjustment cost, washing and sterilization cost and administration cost.
8. When magnifying lens, loops or other attachments are used with the doctors glasses, conventional face shields cannot be used.

SUMMARY OF THE INVENTION

It has now been found that these and other objects of the invention may be attained in a face protector apparatus for protecting the user's face including the eyes, nose, ears or mouth, which includes a web shaped substantially transparent plastic lens member; a frame for mounting on the face of a user including a brow member dimensioned and configured for extending across the face of a user and having first and second axial extremities. The brow member includes depending nose pads for engaging the nose of the user and the frame includes first and second temple members, each of the temple members cooperating with respective axial extremities of the brow member; first and second clips carried on respective temple members, each of the clips including first means for releasably engaging the lens member and independent second means for releasably engaging one of the temple members, the first means releasably engaging the lens without affecting the engagement between the second means and a temple member.

In some forms of the invention each of the second means is slidable along the axial extent of one the temple members. The first means may grip the lens along an edge thereof and the first means may includes a slot for receiving the lens. The first means may include means for locking the lens in the slot and/or a lock screw. The second means may include a lock screw and an elongated slot dimensioned and configured to receive one of the temple members.

In some forms of the invention the clamp is pivotally mounted on the clip and the lens includes a preformed support frame.

In other forms of the invention the apparatus includes means for mounting on the face of a user including a brow member dimensioned and configured for extending across the face of a user and having first and second axial extremities, the brow member including depending nose pads for engaging the nose of the user, the frame including first and second temple members, each of the temple members cooperating with respective axial extremities of the brow member, which includes a web shaped substantially transparent plastic lens member; first and second clips carried on respective associated temple members, each of the clips including first means for releasably engaging the lens member and independent second means for releasably engaging one of the temple members, the first means releasably engaging the lens without affecting the engagement between the second means and a temple member. Each of the second means may be slidable along the axial extent of one of the temple members and the first means may grip the lens along an edge thereof.

In some forms of the invention the first means includes a slot for receiving the lens and the first means includes means for locking the lens in the slot. The first means may include a lock screw and the second means may include a lock screw. The second means may include an elongated slot dimensioned and configured to receive one of the temple members and the second means includes a clamp.

In other forms of the invention includes a preformed glassless frame. The frame includes first and second elongated temple members, the temple members each include a first and second axial extremities. The frame further includes a brow member dimensioned and configured to extend across the face of the user. The brow member may include means for engaging the nose of the user including depending first and second nose pads and means for cooperating with the first axial extremities of each of the temple members. The apparatus also includes a web shaped substantially transparent plastic lens member and first and second means each including means for engaging the frame and means for releasably engaging the lens. The means for releasably engaging the lens is independent of the means for engaging whereby the release of the lens does not affect the meas for engaging.

The means for engaging may cooperate with one of the temple members and may be slidable along the axial extent thereof.

BRIEF DESCRIPTION OF THE DRAWING

The invention will be better understood by reference to the accompanying drawings in which:

FIG. 4 is a cross-section view of the second form of the reusable double clip showing a locking set screw pressed against the lens material and a rivet attachment that acts to secure the clip and to allow for partial rotation adjustment.

FIG. 4A is a plan view of the spring loaded double clip.

FIG. 4B is an inside view of the spring loaded double clip, shown in FIG. 4, secured to the temple frame.

FIG. 4C is a side view of the spring loaded double clip as shown in FIG. 4 showing the locking set screw knob.

FIG. 9A is a side view of a seventh form of the invention showing the face protector with a preformed support frame with clips, lens and head cover attached.

FIG. 9B is a cross-section of the preformed support frame shown in FIG. 9A taken along the line 9B of FIG. 9A.

FIG. 9C is a cross-section of the head cover material holder also shown in FIG. 9B.

FIG. 9D is a side view of the inner face of the clip fastened to the support frame and which shows the structure of FIG. 9A in greater detail.

FIG. 9E is a cross-section of the support frame of FIG. 9A with clip and head cover holder attached.

FIG. 9F is an isometric view of the face protector of FIG. 9A with support frame and clips.

DESCRIPTION OF THE PREFERRED EMBODIMENT

Figure 1:
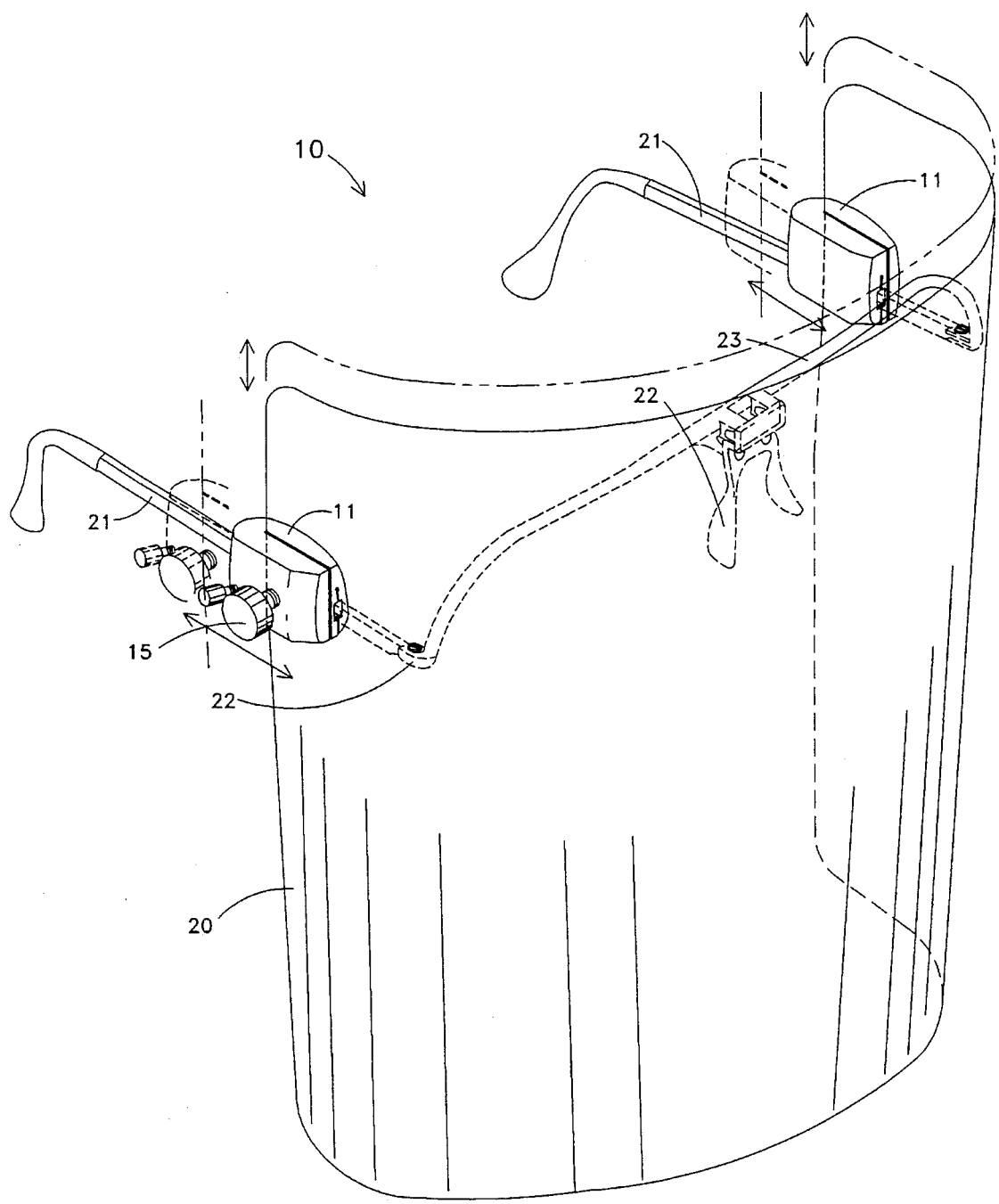
FIG. 1 is a view of one form of the invention showing the glassless support frames with two double clips and a clear plastic face shield lens on a human face.
Figure 2:
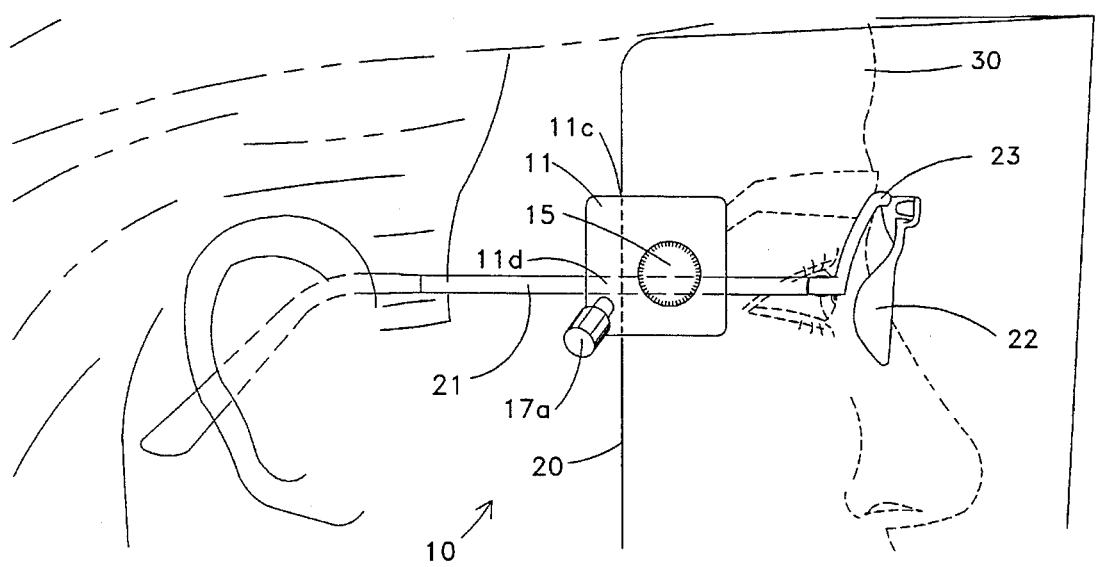
FIG. 2 is a side view showing the side of the frame, clip and lens.
Figure 2A:
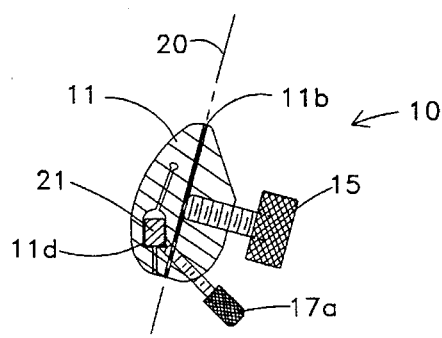
FIG. 2A is a cross-section view of the reusable double clip with a set screw locking feature.
Figure 2B:
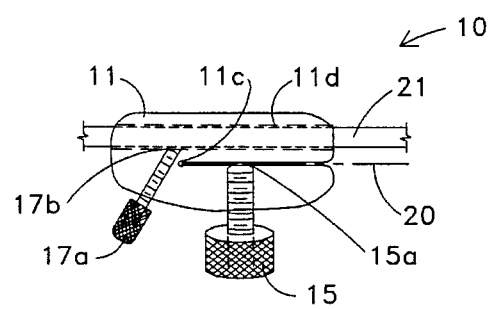
FIG. 2B is a plan or top view of the reusable double clip.
Figure 2C:
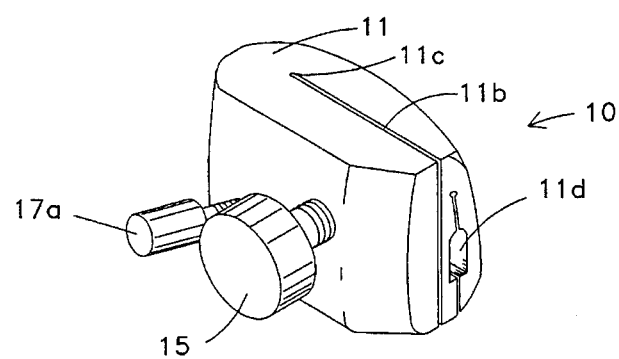
FIG. 2C is an isometric view of the reusable double clip.

Referring now to FIGS. 1 and 2 a face protector 10 is shown that includes a frame that comprises temple members 21, 21 that are pivotally connected to brow member 23 in the manner of conventional glasses. In the usual form of the invention no optical lens or "sunglass" lens (other than the face shield lens 20) is carried on the frame. (Accordingly, the frames may be referred to herein as "glassless" frames.) Carried on the brow member 23 is a pair of nose rests 22. The protector 10 also includes reusable double clips 11, 11 and a clear plastic face shield lens 20. Those skilled in the art will recognize that each double clip 11 is the mirror image of the other. (In certain forms of the invention the cross-section of the temple members or frames 21 may have an interlocking shape for the clips 11.) One such clip 11 is shown in greater detail in FIGS. 2A, 2B, and 2C. The face shield lens 20 is inserted into a slot 11b until it abuts the end 11c of the slot 11b. A lens set screw 15 is shown tightened so that the end 15a of the set screw 15 presses against and slightly deforms the lens 20 and locks it into position. The temples 21 are disposed within respective channel slots 11d and locked in place by the end 17b of a temple set screw 17a.

The slot 11d is dimensioned and configured so that each clip 11 can slide back and forth along the temple 21. The clear plastic face shield lens 20 is inserted into the thin slot 11b in the respective double clips 11 and then secured into position with set screws that lock the lens 20 to the clips 11. Once properly adjusted the clips 11 are then secured into position with set screws 17a that lock the clips onto the temple frames 21. With the clips 11 locked onto the temple frames 21 it is a quick and simple matter to remove and replace a soiled or contaminated face shield lens 20 without further adjustment being necessary.

The face protector 10 may be adjusted to fit any size or any shape head and face. The unique feature of providing both vertical and horizontal adjustment with locking set screws assures a perfect fit every time a new face shield lens 20 is installed. The slot or groove 11d that clamps over the temple frame can be larger than the temple frame cross-section thereby allowing further rotation adjustment that allows the face shield lens 20 to be tilted slightly from the vertical position before being locked into position. The thin slot that the lens 20 is inserted into is tilted inward at the bottom. This causes the face shield to tilt in toward the sides of the chin, tapering down and in for a contoured look that more generally follows the natural tapering of ones head from wide at top to narrow at chin.

The face protector 10, in one form of the invention, also allows for the clips 11, head cover and lens 20 to be attached to a common preformed support frame 5. Once the clips 11 are adjusted to the wearers face and secured to the temple frames 21 of the glassless frame no further adjustments are necessary. Replacement lens 20 are simply inserted in the slot 11b in the support frame 30 and secured with set screws 15. Replacement head covers are simply placed in a holder 31 that is slipped into a slot in the support frame 30 where it also is secured with set screws 32.

This face protector 10 invention comprises a brow member 23, two temple members 21, 21 with two integral reusable double clips 11 and a clear plastic face shield lens 20. The double clips 11 can slide back and forth along the temple frames 21. The clear plastic face shield lens 20 is inserted into the thin slot in the double clips 11 and then secured into position with set screws 15 that lock the lens 20 to the clips 11. Once properly adjusted the clips 11 are then secured into position with set screws that lock them onto the temple frames 21. With the clips 11 locked onto the temple frames 21 it is a quick and simple matter to remove and replace a soiled or contaminated face shield lens 20 without further adjustment being necessary.

The face protector 10 invention can be adjusted to fit any size or any shape head and face. The unique feature of providing both vertical and horizontal adjustment with locking set screws assures a perfect fit every time a face shield lens 20 is used. The slot or groove that clamps over the temple frame can be larger than the temple frame cross-section thereby allowing further rotation adjustment that allows the face shield lens 20 to be tilted slightly from the vertical position before being locked into position. The thin slot that the lens 20 is inserted into is tilted inward at the bottom. This causes the face shield to tilt in toward the sides of the chin tapering down and in for a contoured look that more generally follows the natural tapering of ones head from wide at top to narrow at chin.

The face protector 10 can accommodate a wide range of different shape and thickness face shield lens 20 to suit the protection required for the medical procedure at hand. A full or partial head cover can be utilized with the face shield lens 20 thereby providing even further protection.

The face protector 10 may be used for light duty face protection in a wide variety of applications. It can also act as a secondary protector when worn over safety glasses. The face protector 10, in one form of the invention, also allows for the clips 11, head cover and lens 20 to be attached to a common preformed support frame 30. Once the clips 11 are adjusted to the wearers face and secured to the temple frames 21 and the support frame 30 no further adjustments are necessary. Replacement lens 20 are simply inserted in the slot 11b in the support frame 30 and secured with set screws 15. Replacement head covers 24 are simply placed in a holder 31 that is slipped into a slot in the support frame where it also is secured with set screws.

Figure 3:
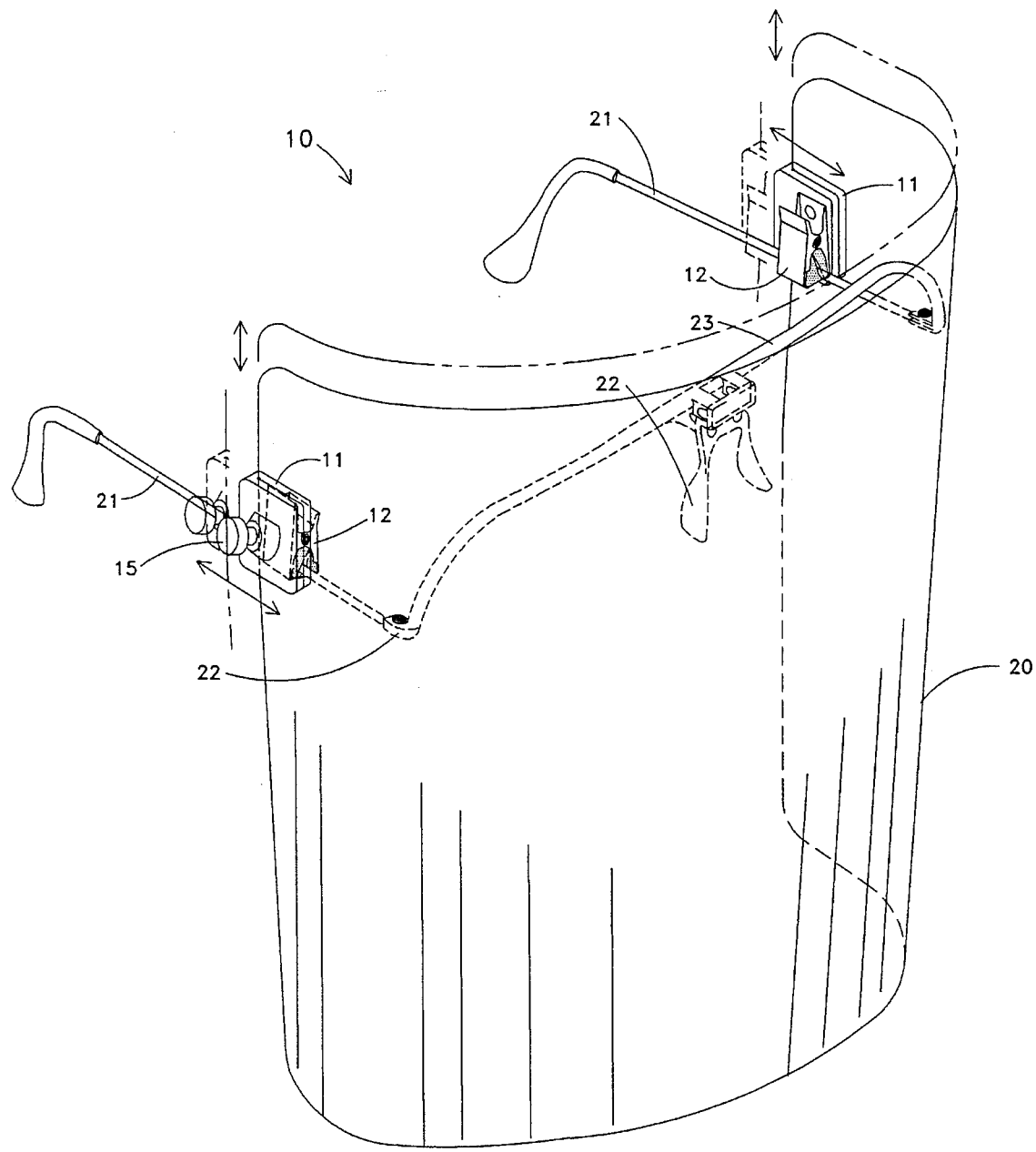
FIG. 3 is a perspective view of the device in accordance with a second form of the invention that includes a double clip with a spring loaded press on clip for connection to the frame.

In another form of the invention, shown in FIGS. 3 and 4, a face protector 10 is shown as above except a clamp on double clip 11 is used. A cushioned grip 14 of the spring loaded clip 12 portion of the double clip 11 engages the temple 21. A rivet 16 allows for slight rotational adjustment of the spring loaded clip 12 portion.

Figure 5:
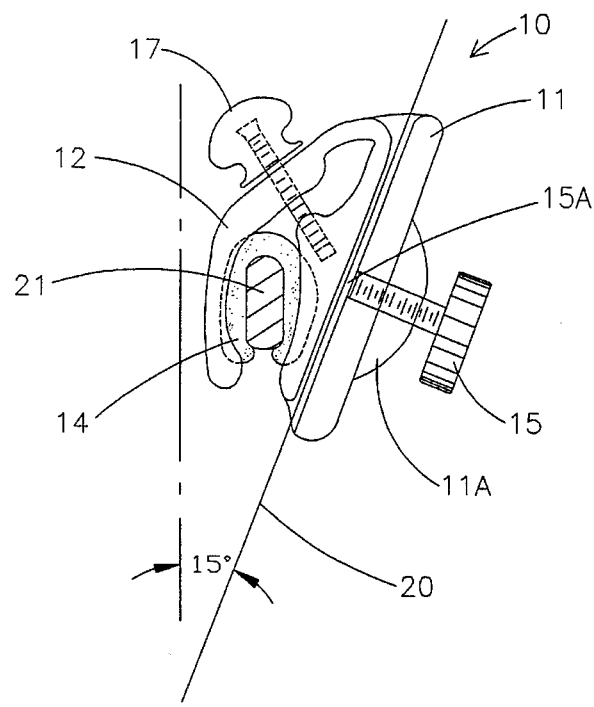
FIG. 5 is a schematic view of a third form of the double clip that shows a screw type clamping action to lock onto the frame.

FIG. 5 shows another form of the double clip 11 with a screw type clamping feature. A set screw 17 provides the necessary clamping action.

Figure 6:
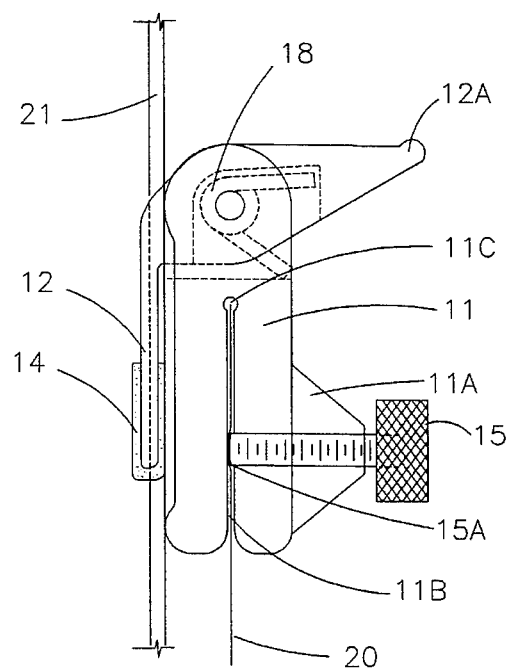
FIG. 6 is a schematic view of fourth form of the double clip that shows a spring loaded clamping action to lock onto the temple frame.

FIG. 6 shows another form of the double clip 11 that shows a spring loaded clamp 12 securing the temple frame 21.

Figure 7:
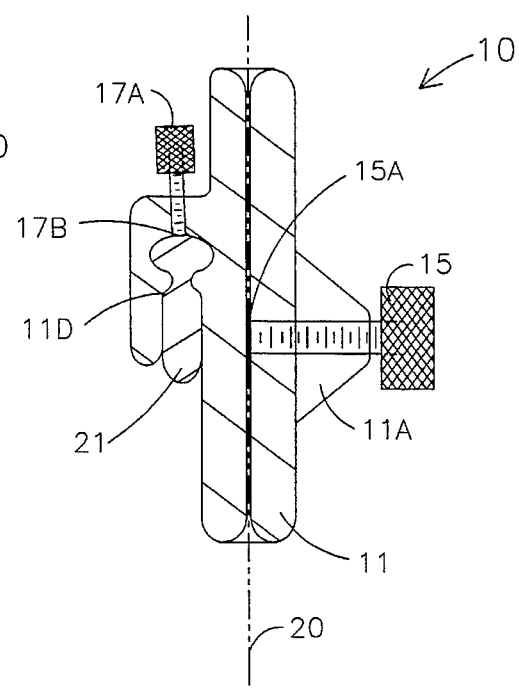
FIG. 7 is a schematic view of fifth form of the double clip that shows part of a frame having a round temple member that allows for rotation adjustment of the clip.

FIG. 7 shows another form of the double clip 11 with a round temple frame 21 that allows for rotation adjustment of the double clip 11 around the temple frame 21.

Figure 8:
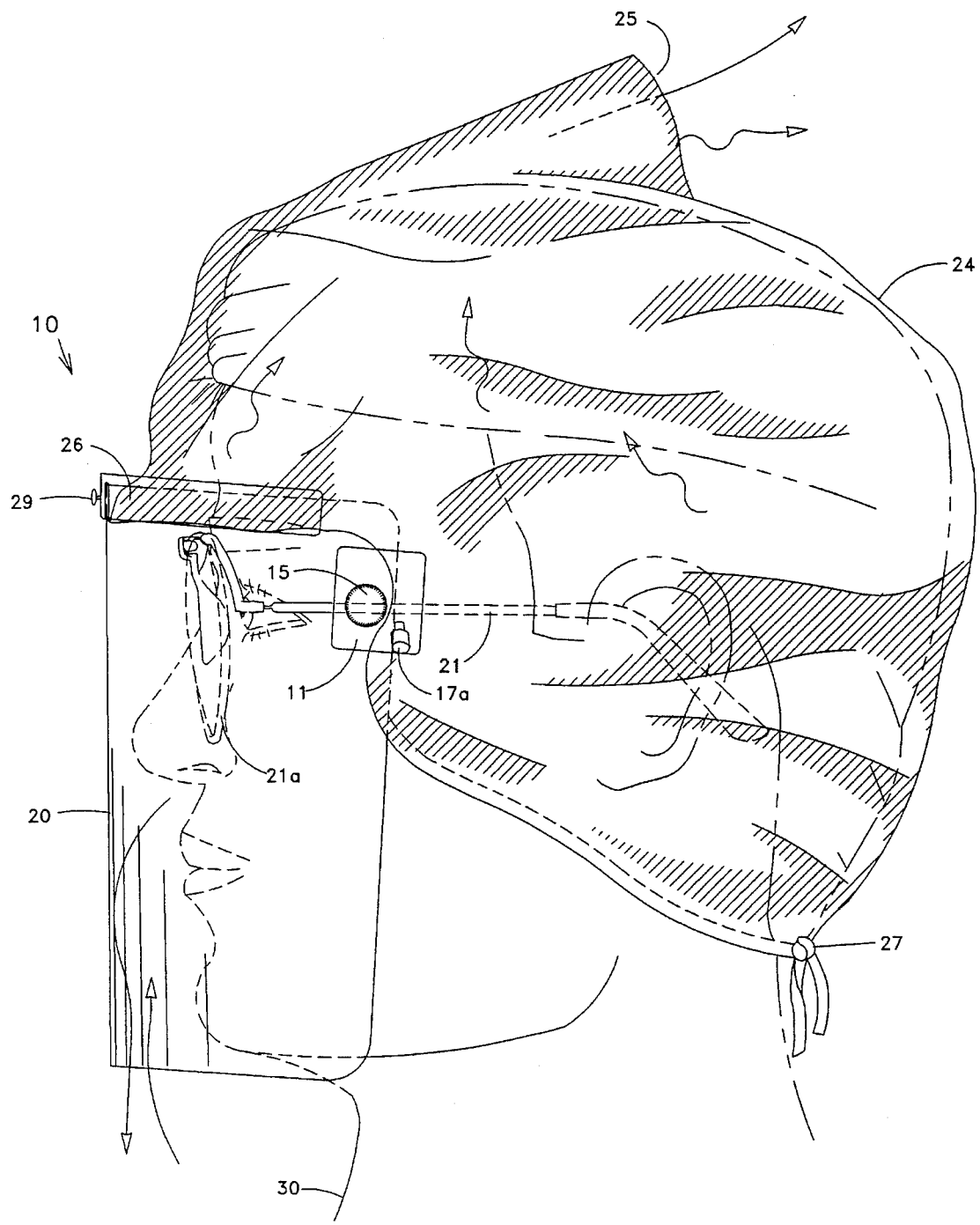
FIG. 8 is a side view of a sixth form of the invention that includes a head cover attached to the face shield lens by means of a clamp device.
Figure 10A:
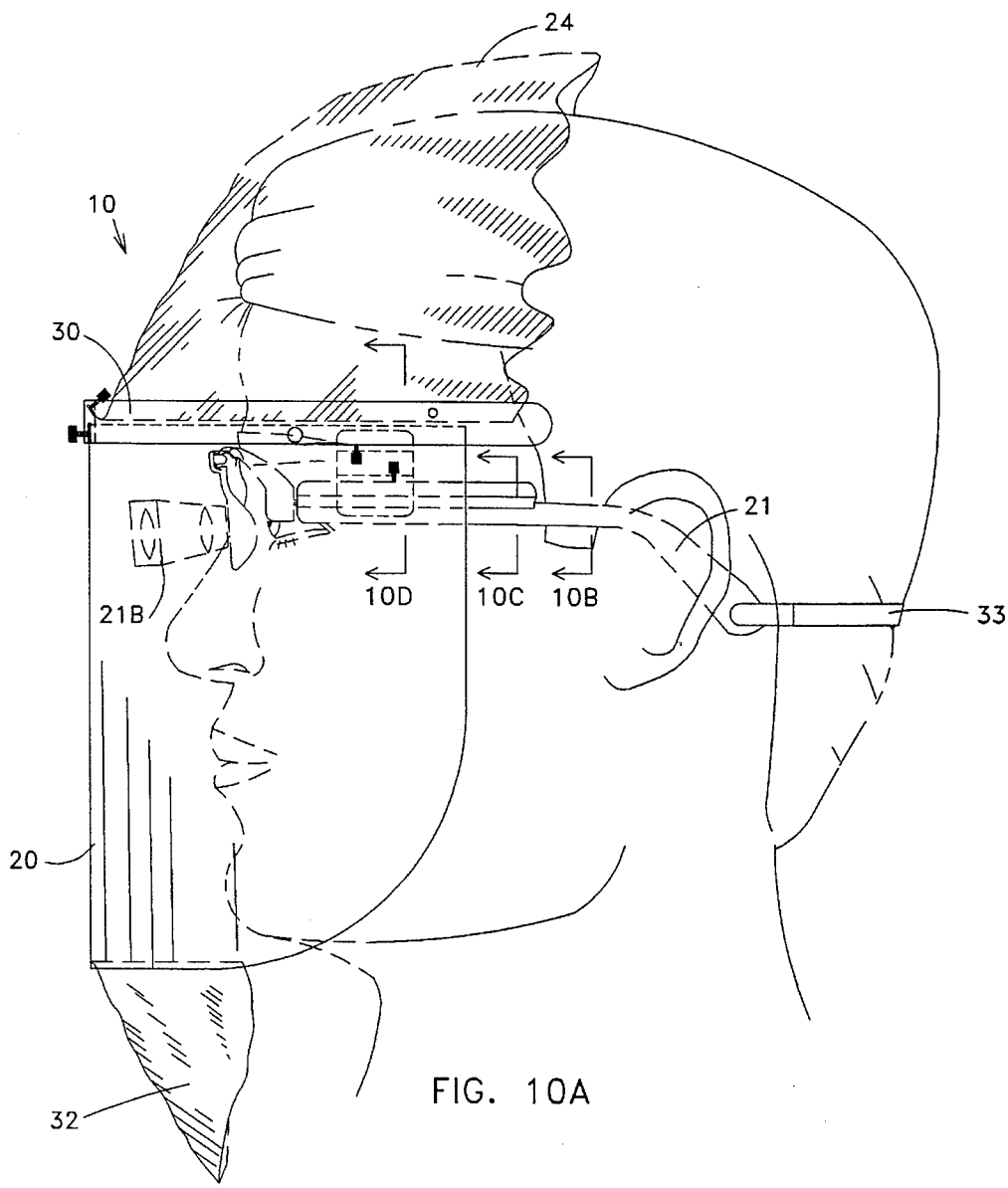
FIG. 10A is a side view of one form of the invention showing the face protector with preformed and integrated support frame, interlocking clips and interlocking temple frames, with lens and head cover attached.
Figure 10B:
FIG. 10B is a cross-section of the temple frame.
Figure 10C:
FIG. 10C is a cross-section of a portion of the preformed temple frame with interlocking matching shape for clip engagement and fastening.
Figure 10D:
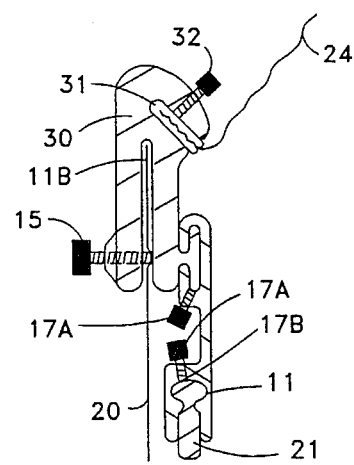
FIG. 10D is a cross-section of the preformed support frame shown in FIG. 10A taken along the line 10C of FIG. 10A. This view shows interlocking of double clip to both the support frame and temple frame.

FIG. 8 shows another form of the face protector 10 with a head cover 24 held in place with clamp 29 at support holder 26 that secures the head cover 24 to the face shield lens 20. This view also shows prescription or safety glasses 21A being used.

FIG. 9A–9F shows another form of the face protector 10 with the clips 11 fastened to an integral preformed support frame 30 and the temple frames 21. In this form the clips 11 can slide along the support frame 30 that holds the lens 20 and head cover 24. The support frame 30 acts to hold and stiffen the lens 20 when the lens 20 material is of a thinner thickness or when the lens 20 is wider and extended out to cover the magnifying lens 21b. Such magnifying lens 21b are frequently used in front of glasses 21a. The support frame 30 being of lightweight plastic can easily deform to suit the head width of the wearer.

FIGS. 10A–10D show still another form of the face protector 10 with the clips 11 interlocked and fastened to an integral preformed support frame 30 and the preformed temple frames 21. In this form, the temple frames 21 are of matching cross-sectional shape for interlocking with the clips 11. The clips 11 can then slide along both the support frame 30 and the temple frame 21 for extended adjustment and failsafe operation. A partial head cover 24, partial chin cover 32 and a safety strap 33, to prevent slipping, is also shown.

IMPROVEMENT OVER PRIOR ART

The face protector 10 is a substantial improvement over prior art for the following reasons:

1. Having the face protector 10 with reusable double clips 11 substantially reduces the cost of face protection.
2. The face protector 10 with reusable double clips 11 allow for adjustment of the clear plastic face shield lens 20 in both the vertical and horizontal direction and in certain forms may include a swivel feature thereby providing for infinite adjustment to fit any size head.
3. The two reusable double clips 11 can be securely clamped to the temple support frames 21 once they are adjusted for ideal fit. Then the two reusable double clips 11 and temple support frames 21 act as a face protector 10 ready to receive replacement face shield lens without loosing the ideal adjustment for ones own unique face.
4. This face protector 10 device speeds up lens replacement between patients for avoiding contamination problems.
5. The reusable double clips 11 clips in another form of the invention can be securely clamped to a clear face shield lens and used with ones safety glasses, prescription glasses or glassless supporting frames 21.
6. The two reusable double clips 11 devices can allow for various thickness face shield lens to be used. During certain procedures it may be desirable to use a thicker lens. Likewise a very lightweight lens may be used on low risk procedures.
7. The face protector 10 device provides such a simple, inexpensive, comfort able and easy to use face shield method that it will be used.
8. The reusable double clips 11 device allows for face shields with light ray shielding properties to be used during certain procedures.
9. The face protector 10 device can also be used with a shorter shield lens for use by the dental patient during certain procedures for protection from dropped instruments, splash or spray.

10. The face protector 10 device can be manufactured out of a lightweight high temperature resistant plastic or metal so that the entire assembly can be sterilized in an autoclave.

11. The face protector 10 device allows for the replacement face shield lens to be supplied in the flat stamped position so that a great quantity can be stacked for packaging and shipping.

12. The face protector 10 device can also be adjusted with the reusable double clips 11 in a forward position thereby allowing the use of loops, magnifying lens or other visual aids behind the face shield lens. This feature also keeps the complex and expensive magnifying lens equipment clean and free of splatter. These units are very difficult to clean and sterilize. The face protector 10 can protect these units from contamination as the doctor goes from patient to patient.

13. The face protector 10 device with glassless temple frames 21 can also be provided with reusable double clips 11 with a channel feature or prongs that allows for the face protector 10 to simply fit over regular glasses.

14. The face protector 10 device with the integral preformed support frame allows for the clips 11, head cover and lens to all be quickly and independently attached to a common support 30. The support frame 30 allows for further extension of a lighter and wider face shield lens as may be used when magnifying lens, as described in item 12 above, are used. The support frame 30 acts to hold and stiffen the wider and lighter weight lens and prevents it from swaying or shaking.

The preformed support frame 30 is partially flattened from the round curvature in front so that glare is reduced at the lens 20, especially when in the extended position. The support frame 30 can thus support any width of thickness lens.

The support frame 30 becomes a convenient universal support and may also be fitted with various attachments including magnifying lens, loops, light shielding lens, a clamp on light, a fan, a nose bridge support and temple frame extensions for resting on ones ears.

The face protector 10 device with integral preformed support frame 30, preformed temple frames 21 and interlocking clips 11 can be adjusted to reduce the face protector weight on the bridge of the nose. When the clips 11 are slid back, toward the ears, the weight also shifts to the non-sensitive ear area. Very little weight, except for support stabilization then occurs at the sensitive bridge of the nose area and forehead area.

FORMS AND VARIATIONS OF THE INVENTION

The face protector 10 may be provided in a number of forms and variations including the following:

1. The face protector 10 may include a glassless support frame with two reusable double clips 11 attached to the temple frames 21. In this form of face protector 10 the face shield lens 20 can be simply attached or replaced without loosing adjustment.

2. The face protector 10 may include prescription, or safety glasses 21A with two reusable double clips 11 attached to the temple frames 21.

In this form of the face protector 10 the face shield lens can also be simply attached without loosing adjustment, but in addition, the wearer has the added protection of his safety glasses 21A. The wearer also has the comfort of using his own comfortable frames.

3. The reusable double clips 11 may be made out of plastic with a thin slot to receive the thin face shield lens. A screw type fastener could be used to tighten against the lens material thereby locking it in place. An attached spring loaded clip 11 could be an integral part of the assembly. This clip portion would be used to clamp onto the temple members 21 of the users glasses.

4. The reusable double clips 11 may be plastic injected molded wherein a portion of the assembly is designed to allow a clamping action to occur so as to clamp onto the temple frames 21.

5. The reusable double clips 11 may be an integral or added part of the temple frames 21. This version may include greater adjustment, and easier manufacturing. This version may also have preformed partially rounded temple frames 21 that allow for partial rotation around frame 21. A swivel feature may also be provided allowing the clip and lens portion to be tilted from the vertical position.

6. The face protector 10 may also include additional clamps that can act to hold a head cover in place.

7. The reusable double clips 11 may be preformed and shaped to match the cross-section shape of the preformed temple frames 21. The clip 11 can then slide along the preformed temple frame 21 without the possibility of becoming disengaged.

8. The reusable double clips 11 may include an offset bracket and swivel that allows for the lens portion to be tilted upward when in the non-protection mode.

9. The reusable double clips 11 may include spring type clamps, press or friction fit clamps, screw type clamps or a wide variety of fastening or clamping devises to simultaneously secure both the face shield lens to ordinary or preformed temple frames 21 thereby forming a face protector 10. The variations of form, of materials and of methods may vary widely but these teachings include the method of a support frame 30 such as glasses or glassless support frames 21 so that the only point of contact is the temple or glassless frames resting on the ears and on the bridge of the nose.

10. The face protector 10 device may include a common preformed support frame 30 that allows for simple and quick attachment of the clips 11, head cover and face shield lens. In this form of the invention the clips 11 connect to the temple frames 21 and the support frame 30. The head cover and lens are secured to the support frame 30. This common support frame 30 may also allow for attachment of other devices.

11. The clips 11 will ordinarily be manufactured of metal or high temperature plastic to permit sterilization in an autoclave. Because sterilization may be achieved without an autoclave other materials may be used in other forms of the invention.

In this form of the invention, a thin slot in the body of the support frame 30 can accept the insertion of a face shield lens 20; the lens is secured in place with set screws 15 that press against the lens material within the slot thereby locking the lens in place.

An additional slot in the support frame 30 can accept the insertion of a head cover holder 31; the holder 31 is secured in place with set screws 32 that press against the holder 31 within the slot thereby locking the head cover 24 and holder 31 in place.

An additional grooved slot in the support frame 30 can accept the clips 11 that secure to the temple frames 21; the clips 11 can then slide along the support frame 30 to obtain optimum adjustment, then lock in place with set screws. In this form the clips are very secure and slide along in a snug, fail proof fit.

Once fitted and adjusted to a wearers face the lens and or head cover can quickly and easily be replaced without further adjustments being necessary.

The invention has been described with reference to its illustrated preferred embodiment. Persons skilled in the art of such devices may upon exposure to the teachings herein, conceive other variations. Such variations are deemed to be encompassed by the disclosure, the invention being delimited only by the following claims.

Having thus described my invention I claim:

1. A device for protecting a user's face including the eyes, nose, ears or mouth, which comprises:

a web shaped substantially transparent plastic lens;

a frame for mounting on the face of a user including a brow member dimensioned and configured for extending across the face of a user and having first and second axial extremities, said brow member including depending nose pads for engaging the nose of the user, said frame including first and second temple members, each of said temple members cooperating with respective axial extremities of said brow member;

first and second clips, each of said first and second clips including first means for releasably engaging said lens and independent second means for releasably engaging respective temple members, said first means releasably engaging said lens without affecting said second means for releasably engaging respective temple members, said second means of said first clip and said second means of said second clip are each dimensioned and configured for sliding movement along the axial extent of respective temple members.

2. The apparatus as described in claim 1 wherein:

said first means grips said lens along an edge thereof.

3. The apparatus as described in claim 2 wherein:

said first means includes a slot for receiving said lens.

4. The apparatus as described in claim 3 wherein:

said first means includes means for locking said lens in said slot.

5. The apparatus as described in claim 4 wherein:

said first means includes a lock screw.

6. The apparatus as described in claim 5 wherein:

said second means includes a lock screw.

7. The apparatus as described in claim 6 wherein:

said second means includes an elongated slot dimensioned and configured to receive one of said temple members.

8. The apparatus as described in claim 1 wherein:

said second means includes a clamp.

9. The apparatus as described in claim 8 wherein:

said clamp is pivotally mounted on said clip.

10. The apparatus as described in claim 9 wherein:

said lens includes a preformed support frame.

11. A device for protecting a user's face including the eyes, nose, ears or mouth, for cooperation with eyeglasses having a frame for mounting on the face of a user including a brow member dimensioned and configured for extending across the face of a user and having first and second axial extremities, the brow member including depending nose pads for engaging the nose of the user, the frame including first and second temple members, each of said temple members cooperating with respective axial extremities of said brow member, which comprises:

a web shaped substantially transparent plastic lens;

first and second clips, each of said first and second clips including first means for releasably engaging said lens and independent second means for releasably engaging respective temple members, said first means releasably engaging said lens without affecting said second means for releasably engaging respective temple members, said second means of said first clip and said second means of said second clip are each dimensioned and configured for sliding movement along the axial extent of respective temple members.

12. The apparatus as described in claim 11 wherein:

said first means grips said lens along an edge thereof.

13. The apparatus as described in claim 12 wherein:

said first means includes a slot for receiving said lens.

14. The apparatus as described in claim 13 wherein:

said first means includes means for locking said lens in said slot.

15. The apparatus as described in claim 14 wherein:

said first means includes a lock screw.

16. The apparatus as described in claim 15 wherein:

said second means includes a lock screw.

17. The apparatus as described in claim 16 wherein:

said second means includes an elongated slot dimensioned and configured to receive one of said temple members.

18. The apparatus as described in claim 17 wherein:

said second means includes a clamp.

19. A device for protecting the face of a user which comprises:

a preformed glassless frame, said frame including first and second elongated temple members, said temple members each including an first and second axial extremities, said frame further including a brow member dimensioned and configured to extend across the face of the user, said brow member further including means for engaging the nose of the user including depending first and second nose pads and means for cooperating with said first axial extremities of each of said temple members, a web shaped substantially transparent plastic lens member;

first and second clips, each of said first and second clips including first means for releasably engaging said lens member and independent second means for releasably engaging respective temple members, said first means releasably engaging said lens without affecting said second means for releasably engaging respective temple members, said second means of said first clip and said second means of said second clip are each dimensioned and configured for sliding movement along the axial extent of respective temple members.

* * * * *